United States Patent [19]
Keller

[11] Patent Number: 5,422,684
[45] Date of Patent: Jun. 6, 1995

[54] PROTECTIVE EYEWEAR WITH RETRACTABLE PROTECTIVE SHIELDS

[76] Inventor: David R. Keller, 532 Sunset Ave., Modesto, Calif. 95351

[21] Appl. No.: 872,450

[22] Filed: Apr. 23, 1992

[51] Int. Cl.⁶ .................... G02C 9/04; A61F 9/00
[52] U.S. Cl. .................... 351/41; 351/57; 2/15
[58] Field of Search .......... 351/57, 41, 43, 44, 351/62, 63, 118, 111; 2/13, 426, 430, 439, 440, 442, 15; D29/17; D16/102, 107, 110, 112

[56] References Cited

U.S. PATENT DOCUMENTS

| | | | |
|---|---|---|---|
| 3,254,932 | 12/1966 | Blaney | 2/13 |
| 3,384,903 | 5/1968 | Malcom, Jr. | 2/14 |
| 3,413,057 | 11/1968 | Carmichael | 2/13 |
| 3,505,679 | 4/1970 | Bennett | 2/13 |
| 3,901,589 | 8/1975 | Bienenfeld | 2/13 |
| 4,785,481 | 11/1988 | Palmer, III et al. | 2/13 |
| 5,129,109 | 7/1992 | Runckel | 2/426 |

FOREIGN PATENT DOCUMENTS

| | | | |
|---|---|---|---|
| 365919 | 2/1982 | Austria | A61F 9/02 |
| 273040 | 9/1913 | Germany | A61F 9/02 |
| 1002915 | 2/1957 | Germany | A61F 9/02 |
| 1138507 | 10/1962 | Germany | A61F 9/02 |
| 481645 | 1/1970 | Switzerland | A61F 9/02 |
| 194164 | 3/1923 | United Kingdom | A61F 9/02 |

*Primary Examiner*—Scott J. Sugarman
*Assistant Examiner*—Darryl Collins
*Attorney, Agent, or Firm*—James J. Leary

[57] ABSTRACT

A form of protective eyewear having retractable eyeshields which protect the wearer's eyes from injury from mechanical, chemical or radiation hazards. The eyeshields have an extended position and a retracted position. In one embodiment, a mechanical actuator moves the eyeshields between the extended position and the retracted position. In another embodiment, the shields contain an inflation chamber which moves the eyeshields between the extended position and the retracted position. The eyewear may be in the form of corrective eyeglasses, sunglasses, safety glasses or safety goggles.

18 Claims, 11 Drawing Sheets

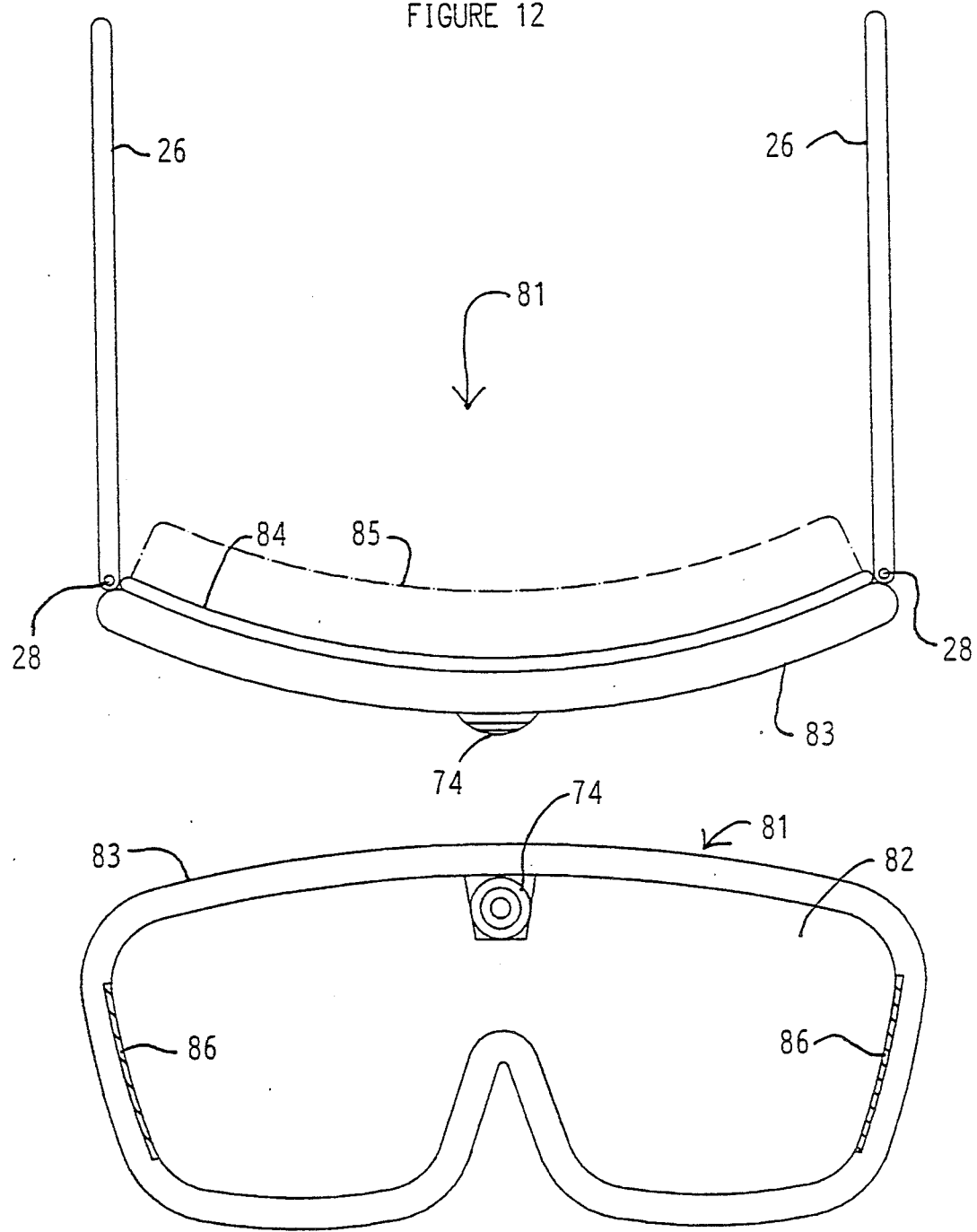

PROTECTIVE EYEWEAR WITH RETRACTABLE PROTECTIVE SHIELDS

This invention relates to an improvement in protective eyewear. More particularly, it relates to a new form of eyewear with retractable protective shields that transform an ordinary pair of eyeglasses into protective safety glasses.

BACKGROUND OF THE INVENTION

The use of protective eyewear is well known in many fields. Different varieties of protective eyewear are worn to protect the eyes from different hazards, such as mechanical injury, chemical damage or radiation exposure. Increasing levels of protection against mechanical injury are afforded by ordinary safety glasses, safety glasses with sideshields and safety goggles. Protection from chemical damage is also available at different levels with safety glasses with splash shields to protect against liquid chemicals splashing into the eyes and sealed safety goggles which also protect the eyes from vapors and fumes. Different levels of protection from radiation exposure are provided by ordinary sunglasses that protect from direct sunlight exposure, wraparound sunglasses that also protect from sunlight exposure from the sides, so-called glacier glasses with very dark lenses and opaque sideshields, welding goggles, laser protection goggles and lead filled safety glasses for protection from x-rays.

One problem that is apparent from a consideration of these different kinds of protective eyewear is that the more protection they provide, the more uncomfortable, more inconvenient and the less versatile they become. The discomfort and the inconvenience often make people reluctant to use proper protective eyewear even when it is available. The lack of versatility causes a need for a person to have different types of protective eyewear for different activities.

A special problem is experienced by people who must also wear corrective eyeglasses. They often have to wear two pairs of eyewear simultaneously, the first pair for vision correction, then another pair of safety glasses or goggles over them for safety protection. The usual result is more inconvenience, distorted vision and ill fitting protective eyewear which compromises their intended purpose. Some adaptations have been made to overcome these inconveniences. Corrective lenses can be made of shatter resistant polycarbonate and removable sideshields can be added to make dual purpose safety glasses and corrective glasses. Clip-on darkened lenses and side shades may be added to ordinary eyeglasses to convert them into sunglasses. While these solutions offer an improvement over wearing two pairs of eyewear at once, they introduce the inconvenience of additional parts that may be lost or misplaced. Some removable side shields require special tools for mounting and removal which adds to the inconvenience.

Another disadvantage of most of the prior art in protective eyewear is that they usually are made in a one-size-fits-all model. There is no variation or adjustment for different facial features or different bone structures. The result of this is often an improper fit which causes discomfort or gaps in the protection which compromise the safety of the wearer.

SUMMARY OF THE INVENTION

The objective of the present invention is to overcome the drawbacks of the prior art by providing a versatile form of eyewear that allows ordinary eyeglasses to be transformed into protective eyewear. It is also an objective of the invention to provide the protective features in a form which can be incorporated directly into a pair of eyeglasses with no separate parts that might be lost or misplaced. An additional objective is to provide the protective features in a form that may be retrofitted to a pair of existing eyeglasses to transform them into protective eyewear. A further objective is to provide the protective features in a form where the fit can be adjusted to the individual wearer to provide a maximum of comfort and protection. Yet another objective of the present invention is to provide a form of eye protection that may be attractively integrated into the design of fashion eyewear. Another important objective is to provide one or more embodiments of the invention which may be made of impact resistant materials in order to meet applicable safety standards, such as ANSI Z87.1 standards.

To this end, the present invention provides a form of eyewear with adjustable and retractable protective shields. In different forms, the shields may provide protection from mechanical, chemical or radiation hazards when they are deployed. Because the protective shields are retractable, they may be moved out of the way when the added protection is not needed. The retraction mechanism also allows the protective shields to be adjusted to the individual wearer to assure a proper fit.

A number of advantages accrue from having retractable protective shields incorporated into a pair of eyewear. First of all it allows safety glasses to be designed so that they more closely resemble ordinary eyeglasses. This will make users less reluctant to wear their safety glasses at all times so that they will always have the safety features available when starting hazardous work or entering hazardous areas. For protective shields on sunglasses, it allows the wearer to adjust the position of the shields according to the ambient light conditions. For certain conditions it may be also be advantageous to be able to deploy one protective shield at a time. For instance if the wearer is exposed to a glaring light from one side only and does not want to compromise his or her peripheral vision in the other direction. Such a situation is frequently encountered when one is driving north or south at sunrise or sunset. Other objects and advantages of the invention will be made apparent by the following description and the accompanying drawings.

BRIEF DESCRIPTION OF THE DRAWINGS

FIG. 12 shows a pair of wraparound glasses with inflatable eyeshields, top view.

FIG. 13 shows the wraparound glasses with inflatable eyeshields, front view.

DETAILED DESCRIPTION OF THE INVENTION

Figure 1:
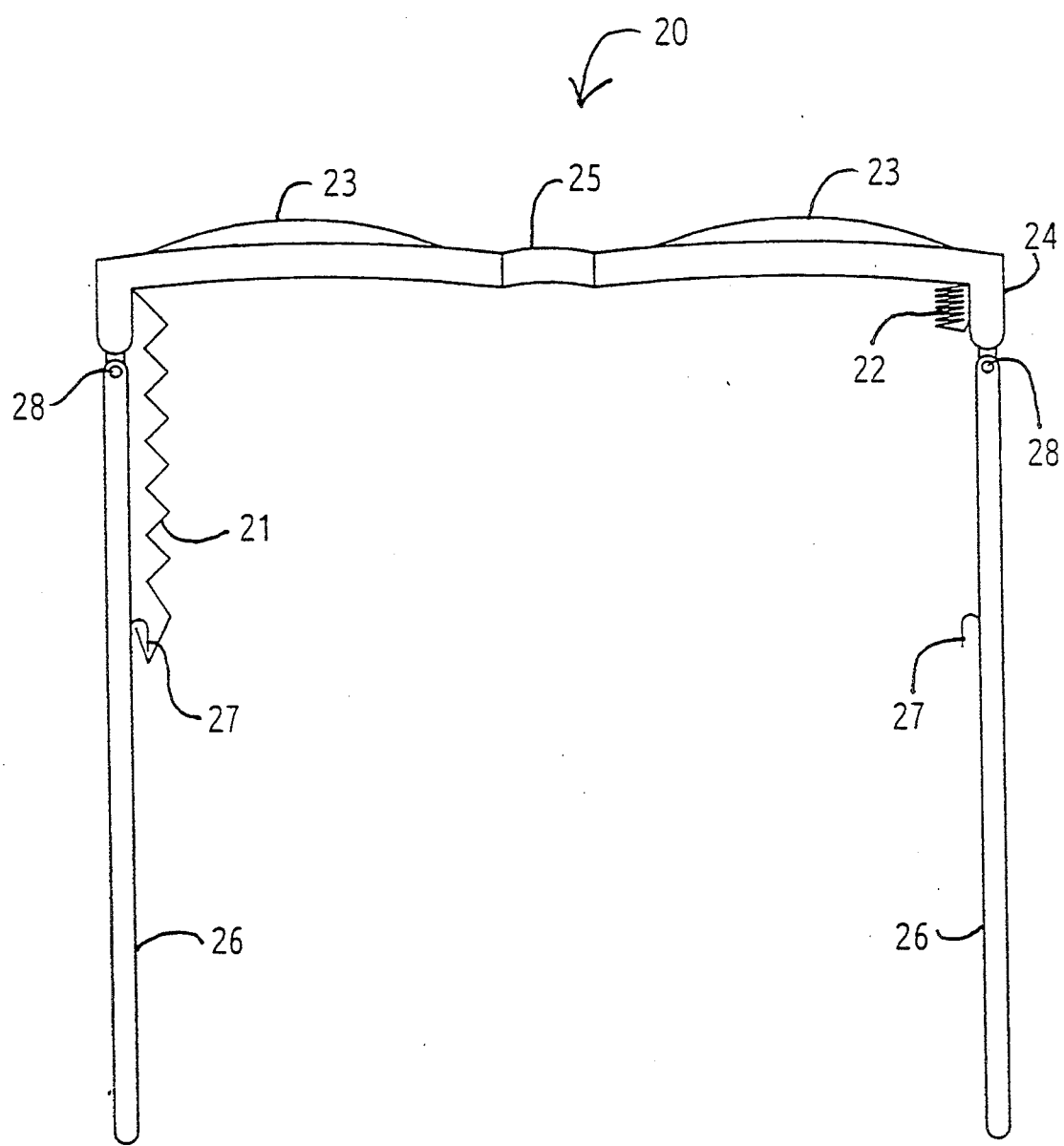
FIG. 1 shows a pair of eyeglasses with folding sideshields.
Figure 2:
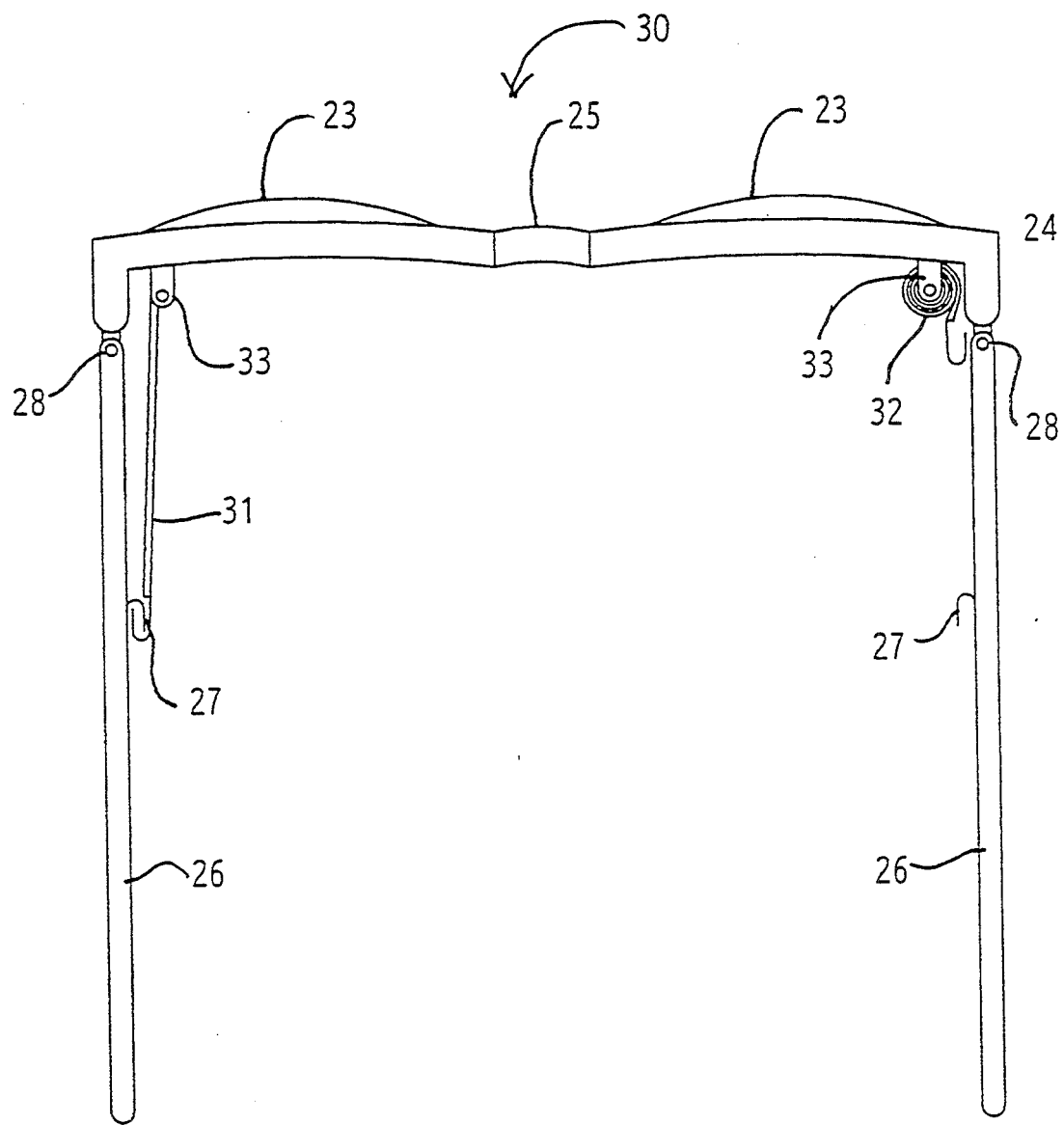
FIG. 2 shows a pair of eyeglasses with roll-up sideshields.

Throughout the figures the following reference numbers remain consistent. The lens(es) is number 23. The frame is number 24. Number 25 is the bride. Number 26 refers to the temple pieces. The hinges are number 28.

FIG. 1

In its simplest form, the present invention comprises a pair of eyeglasses 20 with folding sideshields 21,22. Typically, the eyeglasses 20 have two lenses 23, which may be plano lenses or corrective lenses mounted in a lens frame 24. The lens frame 24 has a bridge 25 which supports the eyeglasses 20 on the nose of the wearer and two temple pieces 26 which are hinged to the lens frame and extend backward to support the eyeglasses on the head or the ears of the wearer. The temples 26 may be straight or curved or may have J-shaped hooks which wrap around the wearer's ears to hold the eyeglasses in place.

Two sideshields 21, 22 attach to the eyeglasses 20 near the outer edges of the lens frame 24 and extend rearward toward the wearer alongside the temple pieces 26. The sideshields 21, 22 may be on the inside of the temples 26 or the outside. The sideshields 21, 22 are made with accordion folds along their length so that they may be adjusted between their extended position 21 and their folded position 22. The end of the side shield 21, 22 may also include an attachment means 27, such as a hook, snap, clamp or slide that holds the side shield to the temple in the folded position, extended position or intermediate positions. In the folded position 21, the sideshields 21, 22 are held adjacent the lens frame 24 so that they do not interfere with the peripheral vision of the wearer. The sideshields 21, 22 are typically rectangular, triangular or oblong in shape and they provide protection from hazards coming from the side of the wearer. The material of the sideshields should be chosen according to the hazards they are intended to protect from. For protection from mechanical or chemical hazards, the sideshields may be made of clear plastic with sufficient impact resistance or chemical resistance to protect the wearer's eyes. For protection from sunlight, the sideshields may be tinted or coated to filter out unwanted radiation.

The hinges 28 which attach the temples 26 to the lens frame 24 are preferably spaced backward from the lenses 23 so that the eyeglasses 20 may be folded without interference from the sideshields 21, 22 when they are in their retracted position. Because of the flexibility of the folding sideshields, the eyeglasses may also be folded when the sideshields are at their extended or intermediate positions.

FIG. 2

A second embodiment of the present invention comprises a pair of eyeglasses 30 with roll-up sideshields 31, 32. The eyeglasses 30 are similar in structure to the eyeglasses in FIG. 1, except that a reel 33 is attached on each side of the lens frame 24 to hold the roll-up sideshields 31,32. The sideshields 31 extend rearward toward the wearer alongside the temples 26 of the eyeglasses 30 to protect the wearer's eyes from hazards coming from the sides. The sideshields may also be made curved so that they give additional protection from the top and bottom of the eyes as well as the sides. When they are not in use, the sideshields 32 may be rolled up on the reels 33 adjacent the lens frame so that they do not interfere with the peripheral vision of the wearer. The reels 33 may have a retraction mechanism, such as a torsion spring, built into them or they may have knobs to aid the wearer in rolling up the sideshields. The sideshields 31, 32 may also have an attachment means 27, such as a hook, snap, clamp or slide that holds the sideshields 31, 32 to the temples 26 in the rolled position, extended position or intermediate positions.

The sideshields are preferably made of a strong, thin and flexible material so that they may be easily rolled up. Clear, tinted or reflective mylar has been found to be ideal for this application. The sideshields are typically rectangular, triangular or oblong in shape. The shape of the sideshields may be integrated into the design of fashion eyeglasses or sunglasses to make them attractive and fashionable. Additional ribs or stiffeners and designs or other visual elements may be added to the sideshields if desired.

As in the first embodiment, the hinges 28 are preferably spaced away from the lens frame 24 so that the eyeglasses 30 may be folded without interference from the rolled up sideshields 31, 32. The flexibility of the sideshields also allows the eyeglasses to be folded when the sideshields are in an extended or intermediate position.

FIG. 3

Figure 3:
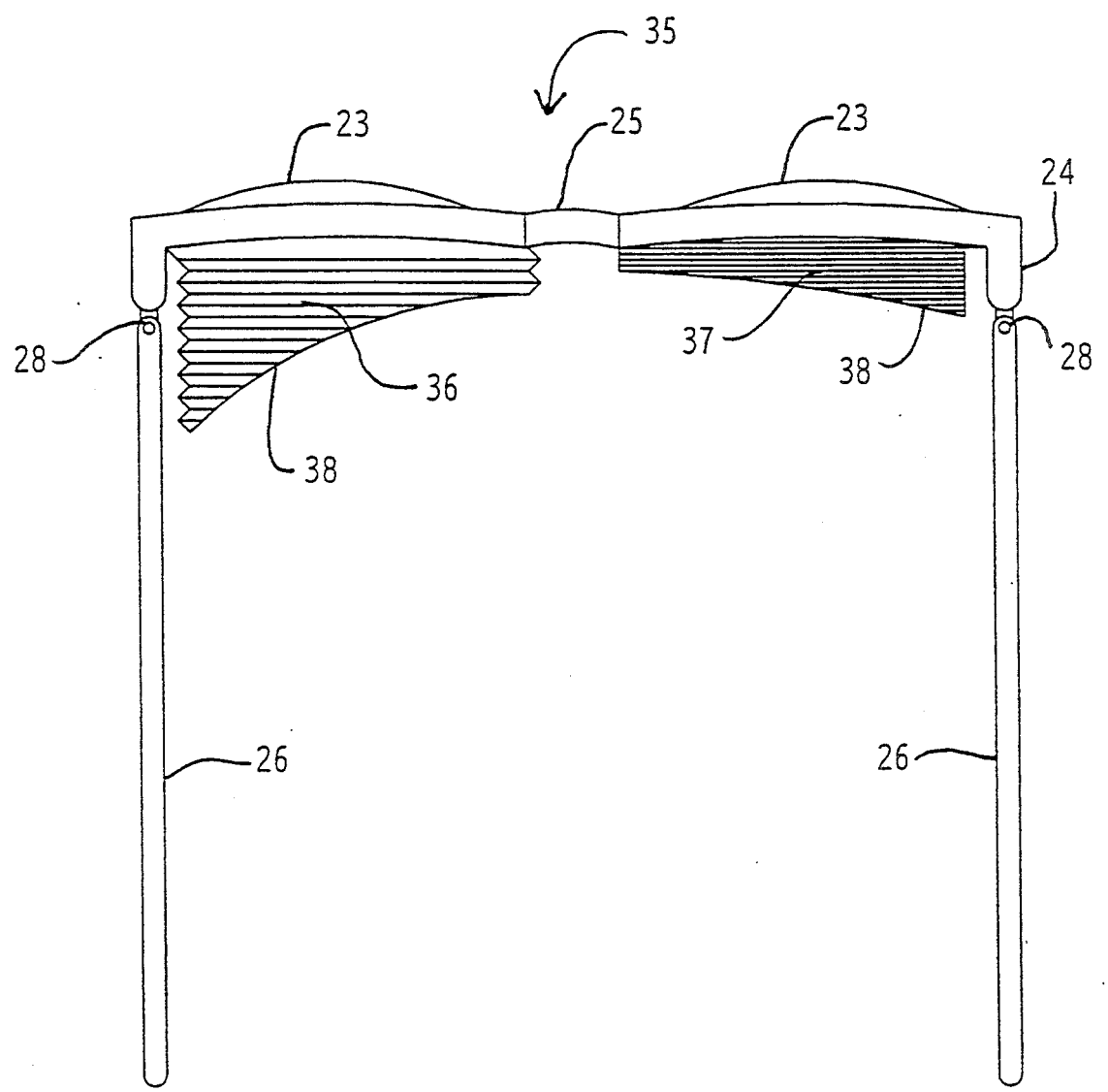
FIG. 3 shows a pair of eyeglasses with folding cup-shaped eyeshields.

For more hazardous situations it is desirable to have protective shields which shield the top and bottom as well as the sides of the eyes from hazards. FIG. 3 shows a pair of eyeglasses 35 with folding eyecups 36, 37 which shield the wearer's eyes from hazards in a full 360 degrees.

The eyeglasses 35 are similar in structure to the eyeglasses in FIG. 1. The protective shields comprise a pair of eyecups 36, 37 which extend between the lens frame 24 and the face of the wearer. The eyecups 36, 37 are contoured to give a close fit against the wearer's face around the eye sockets. The edge 38 of the eyecups 36, 37 may be padded for the wearer's comfort. The eyecups 36, 37 have accordion folds along their length so that they may be folded into a retracted position 37 adjacent the lens frames 24 when their protection is not needed. The accordion folds give another advantage to the eyecups in that it allows them to adjust their shape to the facial contours of the wearer assuring a snug and comfortable fit.

The material of the eyecups should be chosen according to the hazards they are intended to protect from. For protection from mechanical or chemical hazards, the eyecups may be molded from a flexible plastic which has sufficient impact resistance or chemical resistance to protect the wearer's eyes. For protection from sunlight or radiation, the eyecups, as well as the lenses, may be tinted or coated to filter out unwanted radiation. For welding goggles or glacier glasses, the eyecups may be made of a plastic or other material which is pigmented to make it opaque.

The eyecups may be perforated or vented to prevent fogging the lenses. For protection from hazardous fumes and vapors the eyecups may be unvented. The unvented eyecups may be easily retracted to allow venting or to clear fogging when the wearer is away from the hazardous area. The hinges that attach the temples to the lens frame are spaced away from the lenses somewhat so that the eyeglasses may be folded after the eyecups have been collapsed to their retracted position.

FIG. 4

Figure 4:
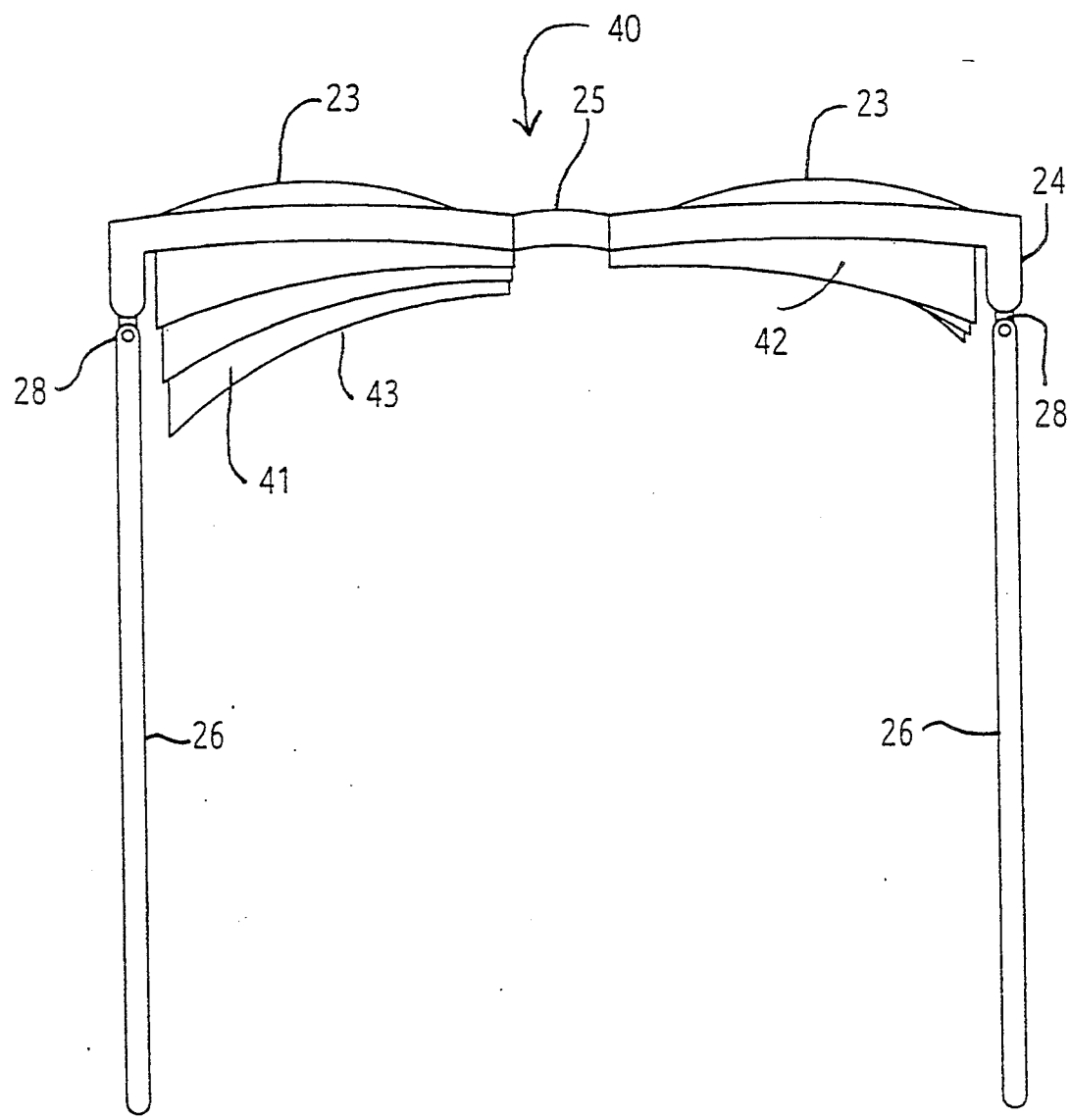
FIG. 4 shows a pair of eyeglasses with telescoping protective shields.

FIG. 4 shows an embodiment of the present invention that comprises a pair of eyeglasses 40 with telescoping rigid protective shields 41, 42. The eyeglasses 40 are of standard construction with two lenses 23 mounted in a lens frame 24. The lens frame has a bridge 25 which supports the eyeglasses 40 on the nose of the wearer and temple pieces 26 which extend rearward to support the eyeglasses on the head or ears of the wearer.

Attached to the lens frame 24 are a pair of protective shields 41, 42 which are made in concentric segments which telescope together. When the protective shields 41, 42 are deployed 41, they extend from the lens frame to the face of the wearer, protecting the wearer's eyes from hazards in a full 360 degrees. When the protective shields are not needed they may be collapsed to a position 42 adjacent the lens frame 24. The telescoping action of the protective shields also allows them to be adjusted for the best possible fit on each individual wearer.

The telescoping protective shields 41, 42 must comprise at least two segments to create the telescoping action. If the shields are made in three segments, as shown, they can be collapsed to a smaller percentage of their extended length. The more segments there are, the smaller the collapsed profile will be. The first segment may be attached to the lens frame 24 or may be made integral with it. Each segment should be made with a detent means so that the shield cannot expand beyond its intended limit. The edge 43 of the final segment may be padded for the comfort of the wearer. The hinges 28 are positioned so that the eyeglasses 40 may be folded after the protective shields 41, 42 have been collapsed to the retracted position.

The segments of the shields are preferably made from an impact resistant plastic, such as polycarbonate. For indoor use, they can be made transparent and for outdoor use or radiation protection, they may be tinted or coated to filter out unwanted radiation. If desired, some or all of the segments may be perforated or vented to allow airflow and to prevent fogging or spaces may be left between the segments forming baffled vents which allow ventilation while excluding hazards from flying particles or splashed liquids.

FIG. 5

Figure 5:
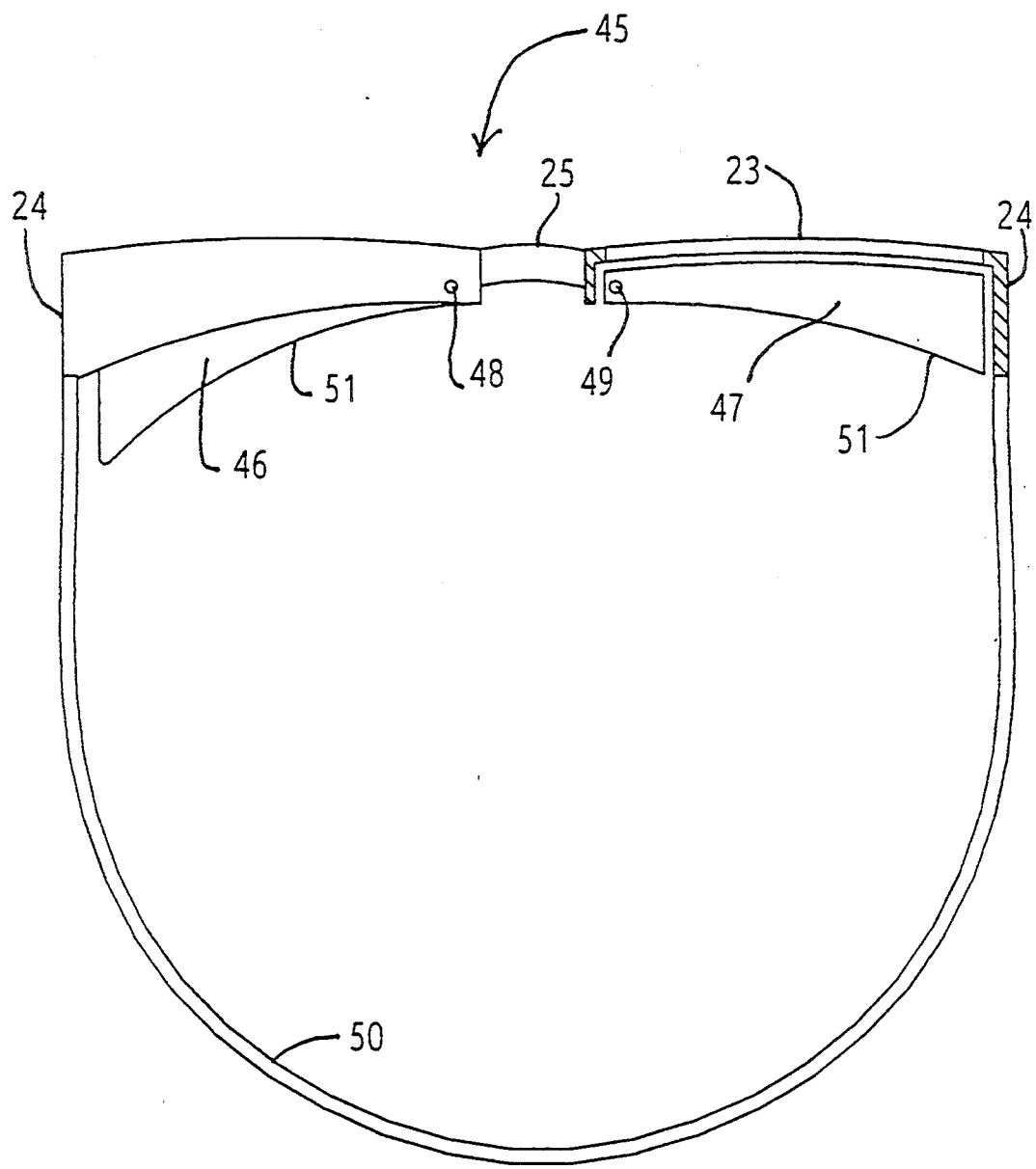
FIG. 5 shows a pair of safety goggles with folding sideshields.

The retractable protective shields of the present invention may also be incorporated into a pair of safety goggles for work hazards or sporting events like skiing. The safety goggles may have one or two lenses set into a lens frame or the lens or lenses may be molded integrally with the frame. By way of example, FIG. 5 depicts a pair of safety goggles 45 having two lenses 23 set into a lens frame 24. The lens frame 24 is fastened to the wearer's head by a head strap 50. The headstrap 50 may be adjustable or elastic to adjust to the size of the wearer's head, and the strap may have a closure means to allow easy attachment or removal of the goggles 45.

The goggles 45 have a pair of protective eyeshields 46, 47 which are attached to the goggles 45 by a pair of pivots 48, 49 near the bridge 25 of the lens frame 24. Like the telescoping eyeshields of the previous example, the pivoting eyeshields 46, 47 may be made in two, three or more segments. The example given shows each of the eyeshields made of two segments. The first segment is made integral with the lens frame and the second segment pivots outward to bridge the distance between the frame and the wearer's face. Thus deployed, the eyeshields protect the wearer's eyes from hazards coming from the top, the bottom and the sides of the eyes. The edge 51 of the pivoting segment may be padded for the comfort of the wearer. When the protection of the eyeshields is not needed, they may be pivoted away from the eyes so that they do not interfere with peripheral vision.

As with the safety glasses in previous examples, the eyeshields of the goggles may be perforated or vented and they may be tinted or coated to exclude unwanted radiation. The lenses and the eyeshields of the goggles are preferably made of a chemical resistant and impact resistant material suitable for their intended use.

Figure 6:
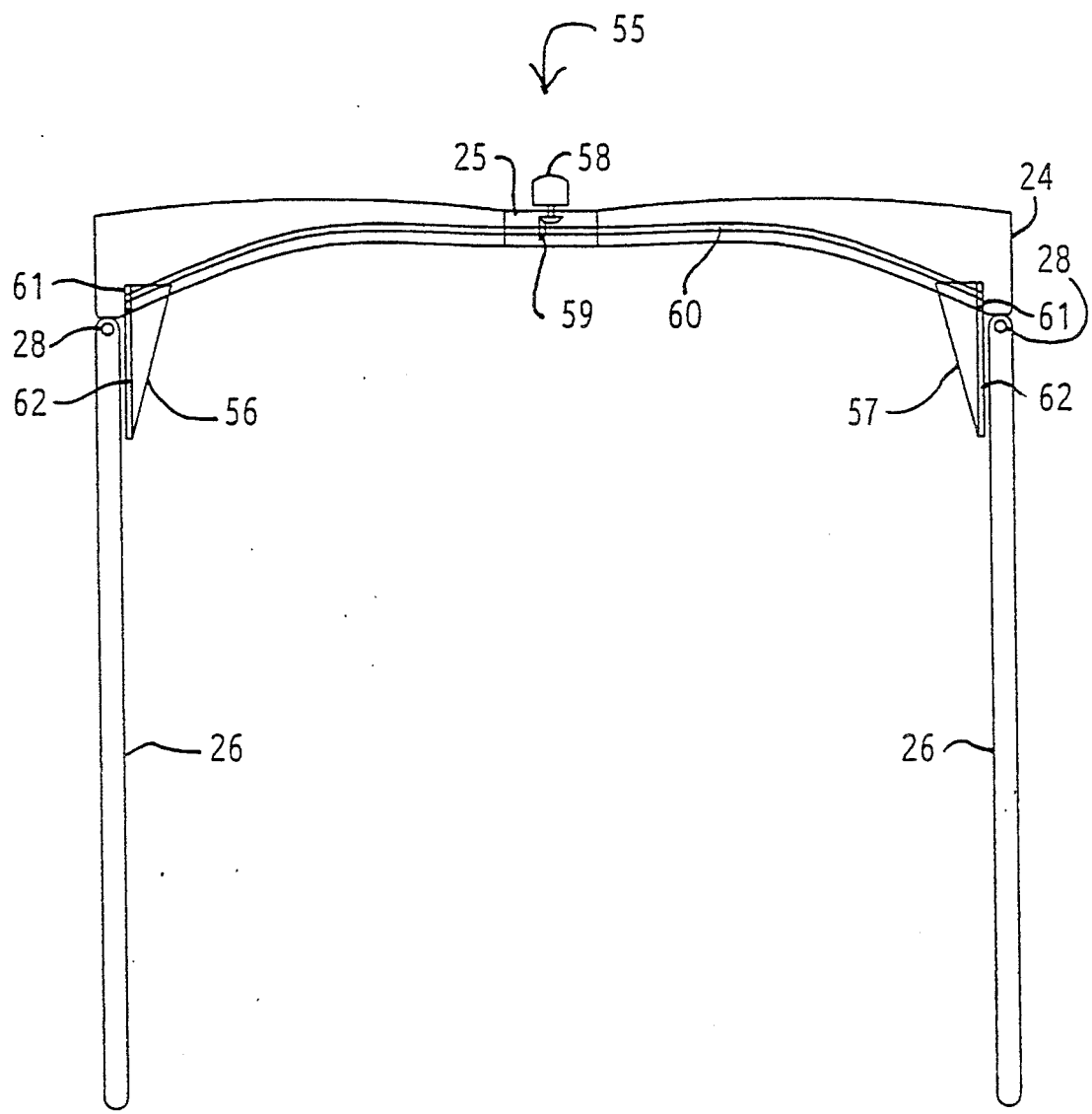
FIG. 6 shows a pair of eyeglasses with mechanically actuated sideshields.
Figure 7:
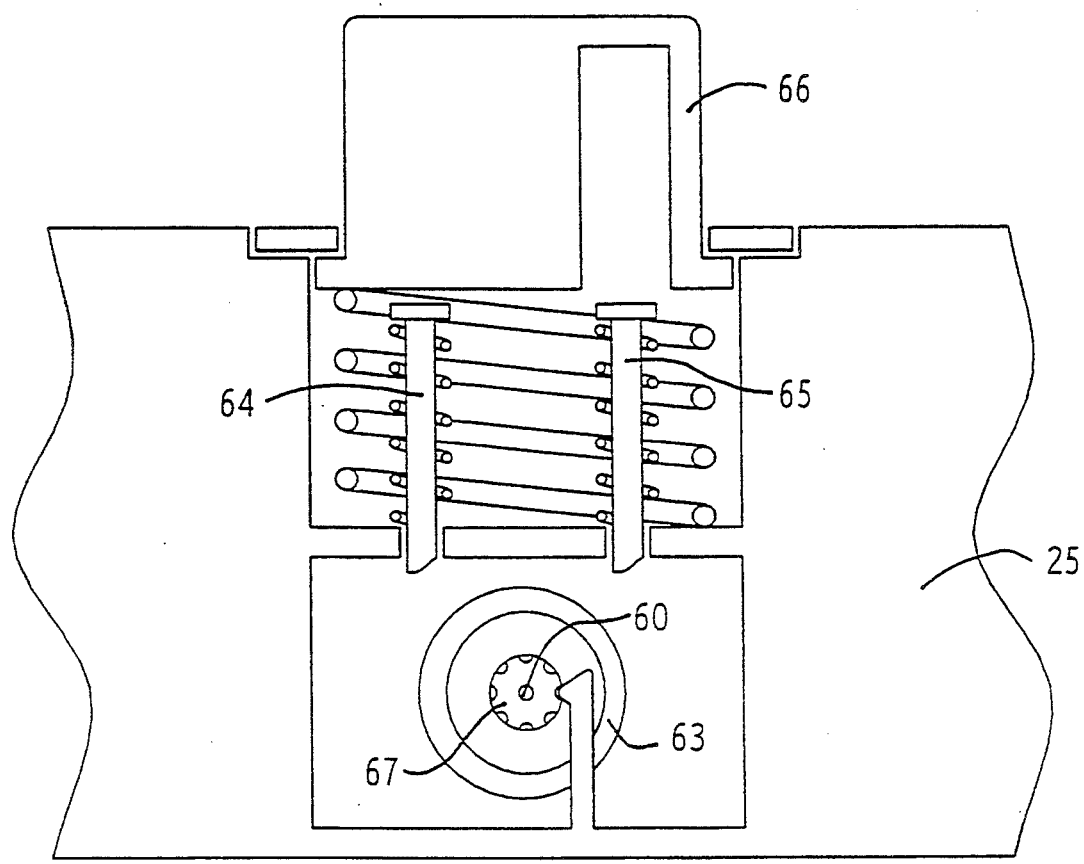
FIG. 7 shows a push button ratchet actuator for sideshields.
Figure 8:
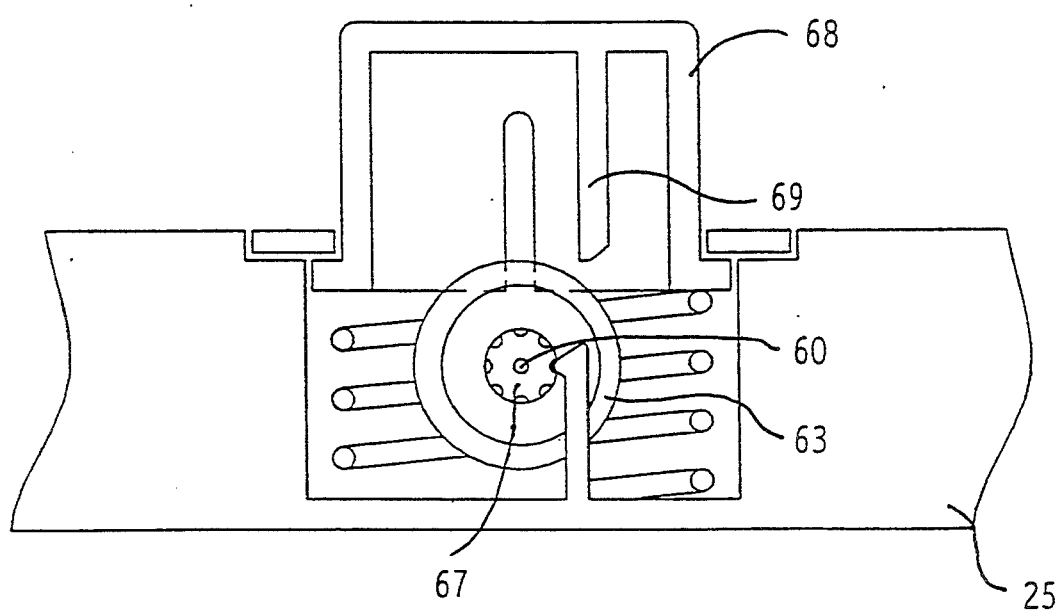
FIG. 8 shows a second push button ratchet actuator for sideshields.

FIGS. 6, 7 and 8

Retractable shields such as these, whether they are incorporated into eyeglasses or goggles, may also include an actuating mechanism to facilitate deployment of the shields. Such a mechanism may be made using levers, gears, screws or other actuators to move the shields into place. An actuator may be incorporated into each side of the eyewear so that each eyeshield may be individually extended or retracted, or a single actuator that operates both eyeshields may be mounted on the bridge or the lens frame. Another application for an actuator would be to connect the two eyeshields with synchronizing gears, or the like, so that when one shield is extended or retracted, the other moves in synchrony.

By way of example, FIG. 6 shows a pair of safety glasses 55 with such a mechanism for mechanical actuation of the protective sideshields 56, 57. The safety glasses 55 have a lens frame 24 which holds the lenses 23 and a pair of temple pieces 26 to support the glasses 55 on the wearer's ears. A pair of retractable sideshields 56, 57 are slidably mounted in guides at the outer edges of the lens frame 24. The sideshields 56, 57 are actuated by a control knob 58 which is connected to a bevel gear 59. The bevel gear 59 drives a flexible drive shaft 60 which in turn is connected to a pair of pinion gears 61 which engage a pair of racks 62 which are molded into the sideshields 56, 57. The sideshields 56, 57 may be extended by turning the control knob 58 in one direction and retracted by turning the opposite direction.

Persons skilled in the mechanical arts will be able to devise other actuating mechanisms to extend and retract the movable sideshields. Two other possible mechanisms that utilize a reversible push button ratchet are shown in FIGS. 7 and 8. In the embodiment of FIG. 7, connected to the flexible drive shaft 60, there is a bidirectional ratchet wheel 63 or a pair of ratchet wheels acting in opposite directions. Two separate ratchet pawls 64, 65 are used to drive the ratchet wheel 63 in one direction or the other. A combined push button and control knob 66 is made so that, when it is pushed in, it forces one of the ratchet pawls 64 into engagement with the ratchet wheel 63. The ratchet wheel 63 turns and, through a flexible drive shaft and rack-and-pinion similar to FIG. 6 or other drive arrangement, it actuates the movable sideshields. The action can be reversed by turning the push button 180 degrees so that it acts on the second ratchet pawl 65. A drag wheel 67 keeps the side shields from moving except when acted on by the ratchet mechanism. Another version of this actuator mechanism is shown in FIG. 8. A combined push button and control knob 68 has a single ratchet pawl 69 molded into it. When the button is pushed the ratchet pawl 69 engages the ratchet wheel 63 and turns it in one direction. The direction of the ratchet may be reversed by turning the button 180 degrees so that the ratchet pawl 69 engages the other side of the ratchet wheel 63.

FIG. 9

Figure 9:
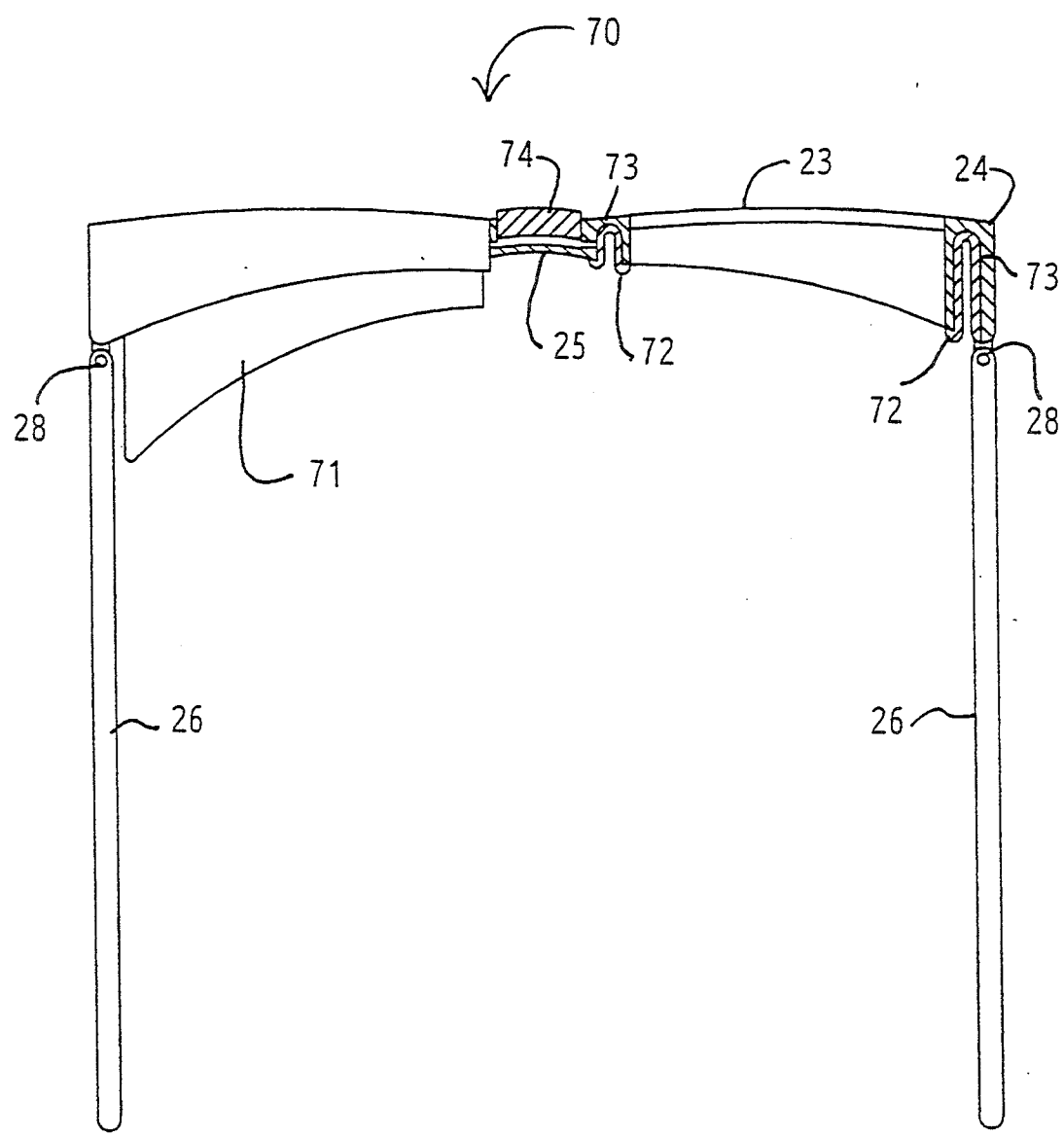
FIG. 9 shows a pair of eyeglasses with inflatable eyeshields.

Another type of retractable protective shield can be made using an inflatable bladder which extends to bridge the space between the eyewear and the wearer's face when it is inflated with air or another fluid. FIG. 9 shows a pair of safety glasses 70 incorporating such a safety device.

The eyeglasses of this embodiment have a pair of lenses 23 mounted in a lens frame 24. Around each lens in the lens frame 24 is an annular recess 73 which serves as an air passage and as a storage space for the inflatable bladders 71,72. Each inflatable bladder 71,72 is sealingly attached to the lens frame 24 along the annular recess 73 surrounding each lens 23. When inflated 71, each bladder is roughly the shape of a truncated double wall cylinder with an inflation chamber 75 between the two walls. The truncated end of the cylinder is contoured so that it fits snuggly and comfortably against the eye socket of the wearer.

The eyeglasses 70 may also incorporate an inflation pump 74 mounted on the bridge 25 or elsewhere on the lens frame 24. Suitable inflation pumps include piston pumps, diaphragm pumps and bulb pumps. Alternatively, the frame may incorporate a connector and a valve so that the eyeshields may be inflated with an external pump, such as a syringe or a squeeze bulb. When the bladder is deflated the eyeshield everts 72 or collapses in on itself so that it is stored inside the annular recess 73 or adjacent to the lens frame 24.

Figure 10:
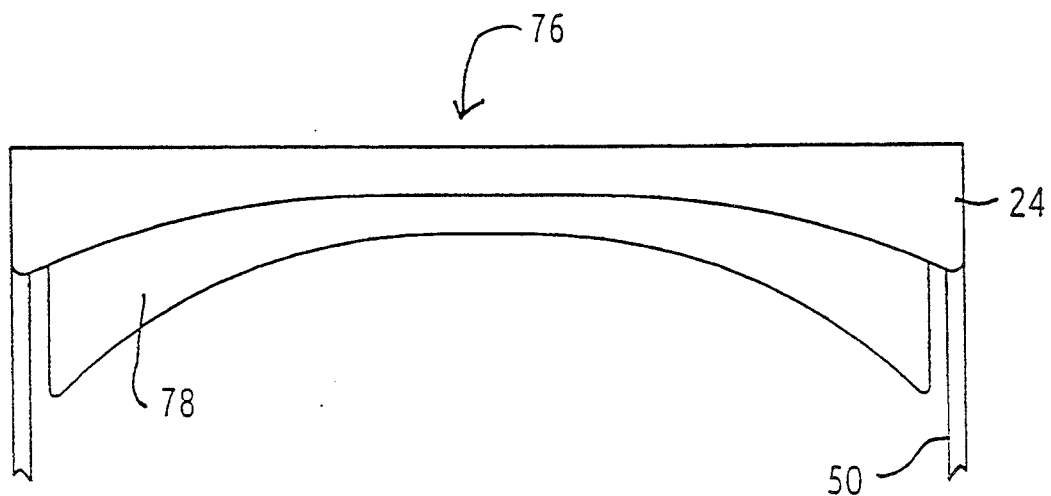
FIG. 10 shows a pair of safety goggles with an inflated eyeshield.
Figure 11:
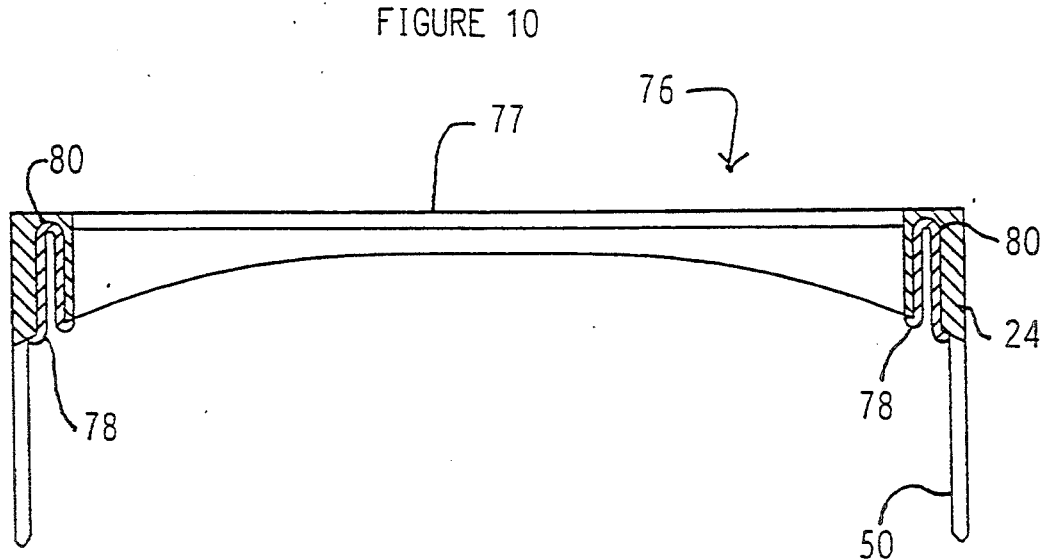
FIG. 11 shows a pair of safety goggles with a deflated eyeshield.

FIG. 10 and FIG. 11

All of the previous examples have been described as having two lenses mounted in a lens frame so that the lenses may be plano or corrective lenses. There may be some circumstances under which it is preferable to have a single lens for both eyes. For instance, when a user prefers to wear his or her corrective eyeglasses underneath a pair of safety goggles, it is easier to make the goggles fit over the glasses if they have one planar lens encompassing both eyes. Also, in recent years fashion eyewear, especially sunglasses, have been made with a single curved lens that covers both eyes. Many of the previously described protective eyeshields may be adapted for use with a single-lens pair of goggles or eyeglasses.

By way of example, FIGS. 10 and 11 show a pair of safety goggles 76 with a single plano lens 77 and an inflatable eyeshield 78 that surrounds both eyes. FIG. 10 shows the lens frame 24 of the goggles 76 with the inflated eyeshield 78 extending rearward to bridge the space between the lens frame and the face of the wearer. The inflated eyeshield 87 is roughly the shape of a truncated, oval double walled cylinder with an inflation chamber 87 between the two walls. The truncated end of the cylinder is contoured to fit snuggly and comfortably around the eyes of the wearer protecting from hazards from all directions.

FIG. 11 shows a cross sectional view of the goggles with the eyeshield 78 deflated. The eyeshield 78 is sealingly attached to an annular recess 80 in the lens frame 24 which acts as an air passage and as a storage space for the eyeshield 78. When the eyeshield 78 is deflated, everts or collapses inward and is stored in a retracted position inside the annular recess 80 or adjacent the lens frame 24 of the goggles 76. As for the inflatable safety glasses of the previous example, an integral inflation pump or a connection means for attaching an external inflation pump may be provided. A headstrap 50 or other means is provided for attaching the goggles 76 to the user's head.

Figure 14:
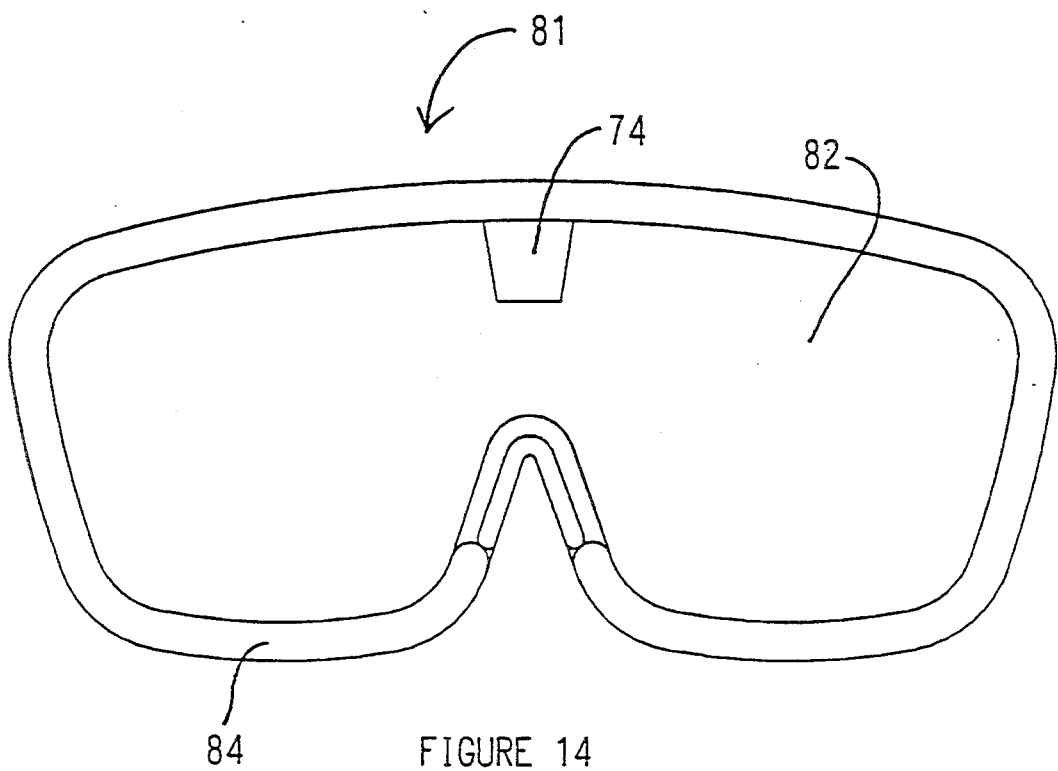
FIG. 14 shows the wraparound glasses with inflatable eyeshields, rear view.

FIGS. 12, 13 and 14

FIGS. 12, 13 and 14 show a variation of the inflatable retracting protective shields adapted to a pair of fashion eyewear. In this example the eyewear 81 has a single unitary lens 82 which is curved to match the curvature of the wearer's face. This style of "wraparound" glasses has become quite popular in fashion sunglasses and safety glasses, and is starting to become available in prescription glasses as well. A frame 83 surrounds and supports the lens 82. A pair of temple pieces 26 are hinged to the frame 83 and project rearward to support the eyewear on the head or the ears of the wearer. In order to give the eyewear the full protection of a pair of safety goggles an inflatable bladder 84 is attached all along the top, side and bottom rims of the frame facing the wearer, as shown in FIG. 14. As previously described, an inflation pump 74 or an inflation connection may be located on the bridge of the eyewear or elsewhere on the frames. When the bladder 84 is deflated, the eyewear has the appearance of an ordinary pair of fashion eyewear. When the bladder is inflated, as shown by the phantom line 85 in FIG. 12, it extends to bridge the gap between the frames and the wearer's face to give a full 360 degrees of protection from mechanical hazards, chemical hazards and radiation exposure.

As shown in FIG. 13, vents 86 may be provided along the sides or elsewhere on the frame 83 to prevent fogging of the lens 82. Optionally, a head band which attaches to the temple pieces 26 or J-shaped hooks on the ends of the temple pieces 26 may be used to keep the eyewear firmly seated against the wearer's face to promote a good seal when the bladder is inflated.

CONCLUSIONS, RAMIFICATIONS AND SCOPE

All of the above examples of retractable protective eyeshields have been described as being attached to a pair of eyeglasses or goggles. It can be seen, however, that each of the examples given might also be made as a separate device which includes a means for attaching them to a pair of preexisting eyewear, thereby transforming an ordinary pair of eyeglasses or sunglasses into protective eyewear.

Because of the versatility of the present invention, its features may be incorporated into a great many different embodiments. The examples given are just a few of the possibilities. For instance, there are a great many combinations and subcombinations that could be made using the features described or equivalent structures may be substituted for some of the features. Thus, the examples given should only be interpreted as illustrations of some of the preferred embodiments of the invention, and the full scope of the invention should be determined by the appended claims and their legal equivalents.

I claim:

1. Protective eyewear, comprising:
   a lens frame containing one or more lenses,
   a means for attaching the eyewear to the head of a wearer,
   one or more protective shields attached to said lens frame,
   said protective shields being movable between at least two positions, including a retracted position wherein said protective shields are positioned adjacent said lens frames, said protective shields not obstructing view through said lenses when in said retracted position, and an extended position wherein said protective shields extend from said lens frame toward the wearer.

2. The protective eyewear of claim 1, wherein said lenses and said protective shields are made of a shatter resistant material.

3. The protective eyewear of claim 2, wherein said shatter resistant material is polycarbonate.

4. The protective eyewear of claim 1, wherein said protective shields are tinted or coated to filter out unwanted radiation.

5. The protective eyewear of claim 1 further comprising a mechanical actuator for moving said protective shields between said retracted position and said extended position.

6. The protective eyewear of claim 1, wherein said protective shields comprise a plurality of shield segments arranged to move telescopically from said extended position to said retracted position.

7. The protective eyewear of claim 1, wherein said protective shields comprise at least one shield segment pivotally attached to said lens frame, said shield segment being pivotable from said extended position to said retracted position.

8. The protective eyewear of claim 1, wherein said protective shields are pleated, said protective shields being foldable from said extended position to said retracted position.

9. The protective eyewear of claim 1, further comprising at least one reel attached to said lens frames, said protective shields being rolled on said at least one reel when in said retracted position, and said protective shields being unrolled from said at least one reel when in said extended position.

10. The protective eyewear of claim 1, wherein said at least one lens comprises a single lens which covers both eyes of the wearer.

11. The protective eyewear of claim 1, wherein said lens frame further comprises at least one vent for ventilating the interior of said protective eyewear.

12. A protective device for attachment to a pair of eyeglasses, comprising:
    one or more protective shields,
    a means for attaching said protective shields to said eyeglasses,
    said protective shields being movable between at least two positions, including a retracted position wherein said protective shields are positioned adjacent the lenses of said eyeglasses, said protective shields not obstructing view through said lenses when in said retracted position, and an extended position wherein said protective shields extend from said lenses toward the wearer.

13. The protective device of claim 12, wherein said protective shields are made of a shatter resistant material.

14. The protective device of claim 13, wherein said shatter resistant material is polycarbonate.

15. The protective device of claim 12, wherein said protective shields are tinted or coated to filter out unwanted radiation.

16. The protective device of claim 12 further comprising a mechanical actuator for moving said protective shields between said retracted position and said extended position.

17. Protective eyewear, comprising:
    a lens frame containing at least one lens,
    a means for attaching the eyewear to the head of a wearer,
    at least one protective shield attached to said lens frame, said protective shield comprising an inflatable bladder,
    said protective shield being movable between two positions, including a deflated position wherein said protective shield is positioned adjacent said lens frames and said protective shield is spaced apart from the face of the wearer, and an inflated position wherein said protective shields extend from said lens frame toward the wearer.

18. A protective device for attachment to a pair of eyeglasses, comprising:
    at least one protective shield, said protective shield comprising an inflatable bladder,
    a means for attaching said protective shield to said eyeglasses,
    said protective shield being movable between two positions, including a deflated position wherein said protective shield is positioned adjacent the lenses of said eyeglasses and said protective shield is spaced apart from the face of the wearer, and an inflated position wherein said protective shield extends from said lens frame toward the wearer.

* * * * *